United States Patent
Jacobsen et al.

(10) Patent No.: US 7,628,590 B2
(45) Date of Patent: Dec. 8, 2009

(54) METHOD AND APPARATUS FOR REDUCING FREE FLOW RISK

(75) Inventors: Stephen C. Jacobsen, Salt Lake City, UT (US); Jon Beck, Salt Lake City, UT (US); Christopher Brydon, Salt Lake City, UT (US)

(73) Assignee: Sterling Investments LC, Salt Lake City, UT (US)

( * ) Notice: Subject to any disclaimer, the term of this patent is extended or adjusted under 35 U.S.C. 154(b) by 275 days.

(21) Appl. No.: 11/059,832

(22) Filed: Feb. 16, 2005

(65) Prior Publication Data

US 2006/0182637 A1 Aug. 17, 2006

(51) Int. Cl.
*F04B 49/00* (2006.01)

(52) U.S. Cl. ............. 417/297; 417/19; 417/26; 417/37; 417/43; 417/53; 417/441; 604/151; 604/246; 604/247; 604/249; 604/156; 137/115.13

(58) Field of Classification Search .......... 417/19, 417/44.2, 44.3, 53, 295, 25, 26, 36, 39, 43, 417/131, 142, 145, 297, 299, 440, 441, 199.2, 417/200, 297.5, 298, 301; 604/65, 66, 131, 604/151, 246, 247, 249, 250, 256, 890.1, 604/891.1, 118; 137/115.13
See application file for complete search history.

(56) References Cited

U.S. PATENT DOCUMENTS

| | | | | |
|---|---|---|---|---|
| 2,881,749 A | * | 4/1959 | Pringham | 123/179.12 |
| 2,897,764 A | * | 8/1959 | Herbert | 417/83 |
| 3,650,642 A | * | 3/1972 | Cygnor et al. | 418/26 |
| 3,981,479 A | | 9/1976 | Foster et al. | |
| 4,106,510 A | | 8/1978 | Hakim et al. | |
| 4,447,224 A | * | 5/1984 | DeCant et al. | 604/67 |
| 4,586,536 A | | 5/1986 | Karmel | |
| 4,593,715 A | | 6/1986 | Stich et al. | |
| 4,613,325 A | | 9/1986 | Abrams | |
| 4,622,992 A | | 11/1986 | Sutherland | |
| 4,626,194 A | | 12/1986 | Mills | |
| 4,650,469 A | | 3/1987 | Berg et al. | |
| 5,038,822 A | | 8/1991 | Iwata | |
| 5,039,279 A | | 8/1991 | Natwick et al. | |
| 5,088,983 A | * | 2/1992 | Burke | 604/141 |
| 5,141,509 A | * | 8/1992 | Burton et al. | 600/40 |
| 5,163,465 A | | 11/1992 | King, Sr. | |
| 5,180,287 A | | 1/1993 | Natwick et al. | |
| 5,396,925 A | | 3/1995 | Poli | |

(Continued)

OTHER PUBLICATIONS

Integrated Hydraulics Ltd, 5CK Series Check Valves, Pilot to Close 7-211.C-7-212.D.

(Continued)

*Primary Examiner*—Devon C Kramer
*Assistant Examiner*—Leonard J Weinstein
(74) *Attorney, Agent, or Firm*—Thorpe North & Western LLP

(57) ABSTRACT

A technique for reducing the risk of free flow through a pump is disclosed. The technique includes sensing a pressure difference between the pump inlet and outlet. The pressure difference is mechanically communicated to a flow restricting element. The flow restricting element increases resistance to flow exiting the pump outlet in a relation to the pressure difference present between the pump inlet and pump outlet.

16 Claims, 4 Drawing Sheets

U.S. PATENT DOCUMENTS

| | | | |
|---|---|---|---|
| 5,462,256 | A | 10/1995 | Minick et al. |
| 5,605,545 | A | 2/1997 | Nowosielski et al. |
| 5,618,269 | A | 4/1997 | Jacobsen et al. |
| 5,658,252 | A | 8/1997 | Johnson |
| 6,224,572 | B1 | 5/2001 | Jacobsen et al. |
| 6,494,694 | B2 | 12/2002 | Lawless et al. |
| 6,620,151 | B2* | 9/2003 | Blischak et al. .......... 604/891.1 |
| 6,935,847 | B2* | 8/2005 | Kuyava et al. ............... 417/278 |
| 6,988,356 | B2* | 1/2006 | Hodinot et al. .......... 60/39.281 |
| 7,331,769 | B2* | 2/2008 | Weis et al. ............... 417/199.2 |
| 2003/0065249 | A1* | 4/2003 | Kuyava et al. ................. 600/40 |
| 2006/0264835 | A1* | 11/2006 | Nielsen et al. .............. 604/174 |
| 2007/0021733 | A1* | 1/2007 | Hansen et al. ........... 604/890.1 |

OTHER PUBLICATIONS

Integrated Hydraulics Ltd, 4KD Series Check Valve, Pilot Operated with Decompression Stage 7-201.C-7-202.B.

Integrated Hydraulics Ltd, 4K82(D) & 4KK82(D) Series Check Valves, Pilot Operated—Ball Type 7-191.C-7-192.D.

Integrated Hydraulics Ltd, 4CKD Series Check Valve, Pilot Operated with Decompression Stage 7-163.B-7-164.C.

www.integratedhydraulics.com products.

* cited by examiner

METHOD AND APPARATUS FOR REDUCING FREE FLOW RISK

FIELD OF THE INVENTION

1. Field of the Invention

The present invention relates generally to reducing the risk of free flow through a fluid pump. More particularly, the present invention relates to reducing the risk of externally pressure induced free flow.

2. Background

A critical safety issue in the design of patient infusion systems is the avoidance of free flow through the system. For example, drugs or nutrients are contained in a fluid that is administered to the patient through an intravenous or feeding system by means of a pump. The fluid is supplied to the pump from a reservoir. If the reservoir becomes pressurized relative to the patient's body, for example due to a difference in elevation or from being squeezed, fluid can be forced through the pump. The resulting free flow of fluid can be harmful or even fatal to the patient.

Various different types of pumps are used in the design of infusion systems. For example, peristaltic pumps operate by flexing or deforming a fluid containing tube to create a directional pumping action. Many peristaltic pump systems are arranged so the tubing (e.g., an intravenous tube) may be removed from the pump. When the tube is removed from the pump, however, a free flow condition can easily result. To help prevent this, a line restrictor or manual valve is often included. Manually operated valves are undesirable, however, since they require operator (e.g., a nurse) interaction, and can be prone to human error. Interlocking systems can avoid the requirement for the manual opening and closing of the valve, but are mechanically complex.

Line restrictors can also suffer a number of disadvantages. Typically, they operate by pinching the tubing with a constant force (e.g., using a spring). The pinching action can weaken the tubing and result in partial collapse of the tubing. This can contribute to pumping inaccuracies and material fatigue. The pinching force must also be relatively large to stop free flow, which can increase the required pumping action and reduce lifetime for a battery powered pump. On the other hand, a sufficiently large pressure difference across the line restrictor can still cause free flow. Hence, a line restrictor may only provide limited protection against external pressure induced free flow.

Another approach to reducing free flow risk is to interconnect active valves with the pump. For example, a valve can be synchronized to open only during pump discharge. Such an arrangement can be effective at preventing free flow, but suffers from disadvantages in mechanical complexity and efficiency. For example, additional energy is required from the power source to drive the active valves, thus reducing lifetime for a battery powered pump. The additional complexity can also increase cost.

SUMMARY OF THE INVENTION

It has been recognized that it would be advantageous to develop a simple and efficient means of reducing the risk of free flow through a pump.

The invention includes a method for reducing the risk of external pressure induced free flow through a pump. The method may include sensing a pressure difference between the pump inlet and pump outlet. The method may also include mechanically communicating this sensed pressure difference to a flow restricting element associated with the outlet side of the pump. Finally, the method may include increasing the resistance to flow exiting the pump outlet with the flow restricting element when the inlet pressure exceeds the outlet pressure.

Additional features and advantages of the invention will be apparent from the detailed description which follows, taken in conjunction with the accompanying drawings, which together illustrate, by way of example, features of the invention.

DETAILED DESCRIPTION

Figure 1:
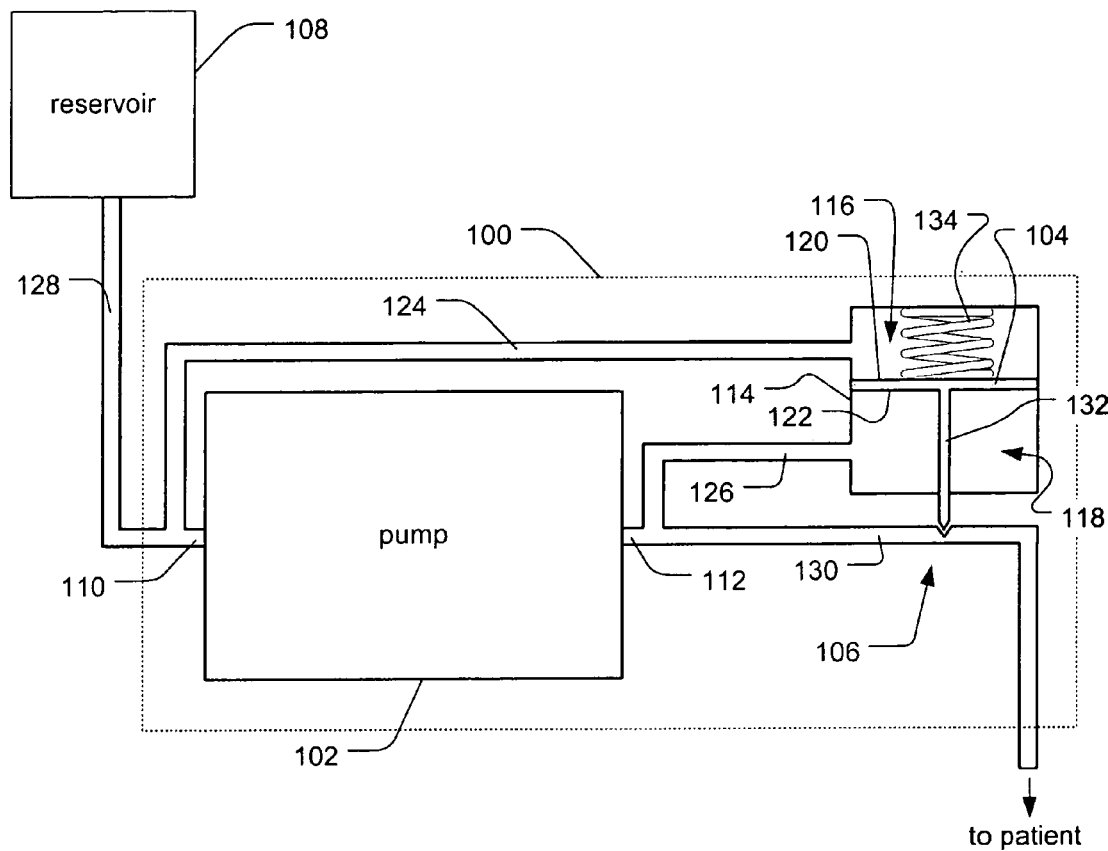
FIG. 1 is a schematic view of an apparatus for reducing free flow risk in accordance with a first embodiment of the present invention.

Reference will now be made to the exemplary embodiments illustrated in the drawings, and specific language will be used herein to describe the same. It will nevertheless be understood that no limitation of the scope of the invention is thereby intended. Alterations and further modifications of the inventive features illustrated herein, and additional applications of the principles of the invention as illustrated herein, which would occur to one skilled in the relevant art and having possession of this disclosure, are to be considered within the scope of the invention.

Referring to FIG. 1, a schematic of an apparatus 100 for reducing free flow risk is shown, in accordance with an embodiment of the present invention. The apparatus is shown in an exemplary application for use in a patient infusion system. Fluid is supplied by a reservoir 108 to a pump 102 via an inlet line 128. The pump has an inlet 110 and an outlet 112, and transfers fluid received from the pump inlet to the pump outlet. The pump outlet 112 is connected to the patient (not shown) via an outlet line 130. Details of the pump are not included here because many different pumps may be used to pump fluid as will occur to one of skill in the art. For example, the pump may be either an active or passive pump, including for example gravity feed intravenous, electrometric, or balloon type pumps.

Coupled to the pump inlet and pump outlet is a pressure responsive member 104, shown here in the form of a moveable piston slidably mounted with a chamber 114. The piston will mechanically respond to a pressure difference between the pump inlet and pump outlet. Mechanically coupled to the piston via a connecting arm 132 is a flow restricting element 106, shown here in the form of a pinch valve.

The chamber 114 is separated into two parts by the piston 104. A first part 116 of the chamber is defined by a first side 120 of the piston, and a second part 118 of the chamber is defined by a second side 122 of the piston. The first part of the chamber is in a pressure transmitting relationship to the pump inlet 110, for example through a first fluid channel 124. The second part of the chamber is in a pressure transmitting relationship to the pump outlet 112, for example through a second fluid channel 126.

The pressure difference between the pump inlet 110 and pump outlet 112 thus causes the piston 104 to translate within the chamber 114, activating the pinch valve 106. For example, when the inlet pressure exceeds the outlet pressure (defined as a positive pressure difference), the pinch valve will constrict the outlet line 130, limiting fluid flow exiting the pump outlet. For example, with increasing pressure difference between the reservoir 108 (and hence pump inlet) and the patient, there will be increased force applied to the pinch valve, tending to reduce limit fluid flow in proportion to the pressure difference.

The force applied to the pinch valve is a function of both the pressure difference and the area of the piston 104 exposed to the first and second parts of the chamber 116, 118. For example, the larger the piston area, the larger the resulting force on the pinch valve 106 for a given pressure difference. Hence, the sensitivity of the piston to the pressure difference can be adjusted by selecting the size of the piston. The piston and pinch valve can be made very sensitive, for example, so as to substantially prevent fluid flow from exiting the pump outlet when the pressure difference is positive. Optionally, a spring or spring-like element 134 may be added to the first part of the chamber 116 to provide a bias shut off threshold if desired. For example, by biasing shut the pinch valve, the valve can be held in a normally closed position (helping to prevent free flow), opening when the pump is actively pumping.

Alternately, a flexible diaphragm can be used in place of the piston 104, where the diaphragm is fixed within the chamber 114, and a portion of the diaphragm moves in response to the pressure differential and is mechanically coupled to the flow restricting element. Additional embodiments illustrating the use of a diaphragm will be discussed further below.

From the foregoing, it will be appreciated that the apparatus provides several benefits. By responding to the pressure difference between the pump inlet and outlet, the apparatus controls free flow based on a root cause of free flow. Enhanced safety is provided because the shut off force of the pinch valve is increased in proportion to the pressure difference, regardless of whether this pressure difference is produce by increased inlet pressure (e.g. squeezing the reservoir) or decreased outlet pressure (e.g. suction on the outlet). This is in contrast to a fixed spring type line restrictor, which provides a constant amount of force regardless of the pressure difference, and thus can be overcome by a high pressure difference. Because the shut off force is increased in proportion to the pressure difference, enhanced efficiency is obtained. When there is no pressure difference, and hence low risk of free flow, the pinch valve has little force applied and thus presents little resistance to flow. This is in contrast to the spring type line restrictor that requires a constant force to overcome, and thus increases resistance to flow and decreases efficiency. This also provides the benefit of allowing the pump to function normally, independent of the inlet to outlet pressure difference.

The use of passive components in the pressure responsive member and flow restrictor also provides additional benefits. For example, little or no additional energy is required from the pump to activate the piston or pinch valve, hence efficiency can be improved over devices using active valves. Fewer moving parts may be needed as compared to active valves, and hence reliability can be enhanced. The relatively simple design can be easier and more economical to manufacture.

Various ways of fabricating the apparatus will occur to one of skill in the art. For example, the pump may be interconnected to the other elements by flexible plastic tubing. Alternately, the pump, pressure responsive member, and flow restrictor may be integrated into a single assembly.

Figure 2:
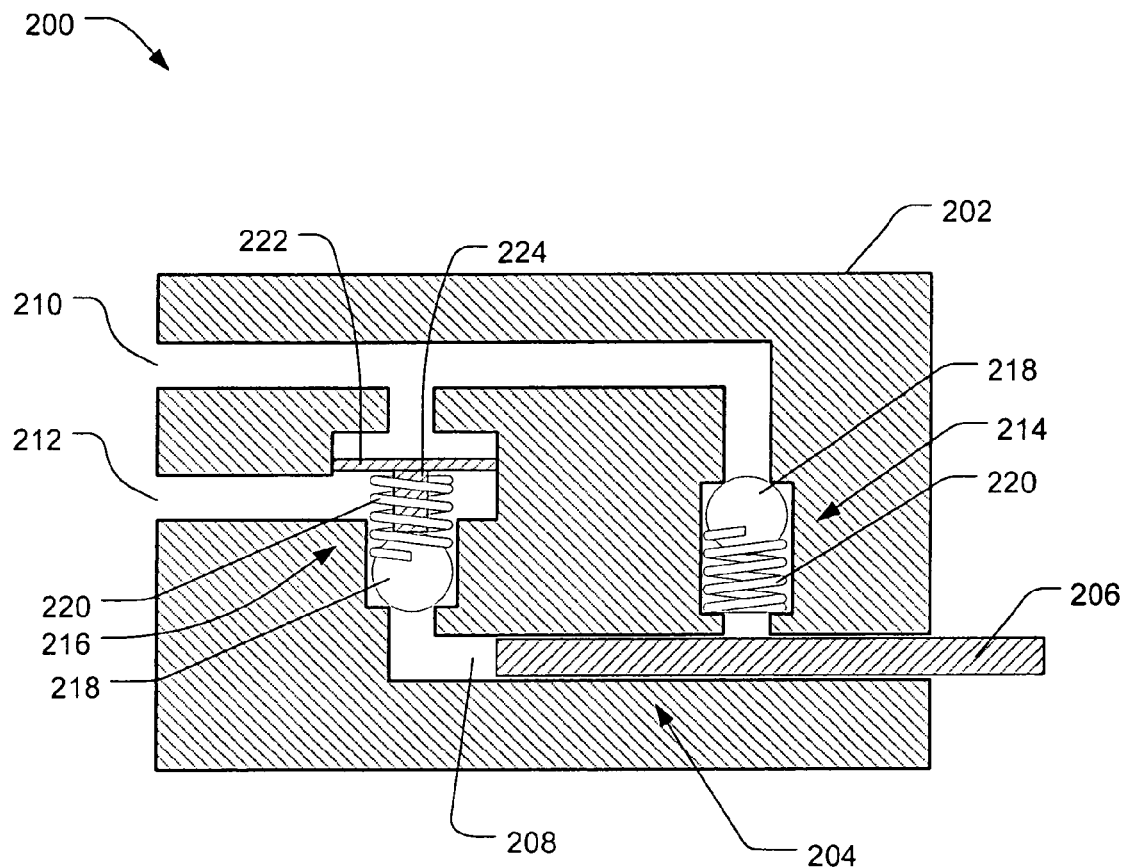
FIG. 2 is a cross-sectional view of an apparatus for reducing free flow risk in accordance with a second embodiment of the present invention.

An alternate arrangement of an apparatus 200 for reducing free flow risk is shown in FIG. 2, in accordance with another embodiment of the present invention. Here, a pump, pressure responsive member, and flow restrictor have been integrated together into a single assembly within a housing 202. The pump 204 is a piston-actuated pump design, wherein a pump piston 206 moves in a reciprocating manner within a pump chamber 208. Fluid is drawn into the pump chamber 208 from an inlet 210 through an inlet check valve 214 when the pump piston is pulled out from the pump chamber, and fluid is ejected through an outlet check valve 216 into the outlet 212 when the pump piston is pushed into the pump chamber. The inlet and outlet check valves are ball valves using a ball 218 and spring 220. The springs provide force on the balls and set the initial cracking pressure of the ball valves. The ball valves provide essentially unidirectional fluid flow from the inlet to the pump chamber, and from the pump chamber to the outlet. For an example of a piston-actuated pump design suitable for use with embodiments of the present invention, refer to commonly assigned U.S. Pat. No. 6,224,572, issued May 1, 2001 to Jacobsen et al., entitled "Piston-Actuated Attachable Topical Fluid Delivery System."

Included in the outlet check valve 216 is a pressure responsive member, shown here in the form of a diaphragm 222. The diaphragm is disposed between the inlet 210 and outlet 212, and includes a connecting arm 224 which bears upon the ball 218 of the outlet check valve. The diaphragm thus mechanically communicates the pressure difference to the outlet check valve. The outlet check valve thus serves as a flow restricting element. As the pressure difference increases, the diaphragm bears with increased pressure on the ball. This has the effect of increasing the cracking pressure of the outlet check valve, functioning to limit fluid flow exiting the pump outlet. Alternately, the diaphragm may be arranged to bear on the spring to produce a similar effect.

As will be apparent from the foregoing, externally induced pressure across the pump 204 (and hence across the pressure responsive member, the diaphragm 222) will have the effect of increasing the cracking pressure of the outlet check valve 216, reducing the likelihood of free flow in proportion to the free flow risk created by the externally induced pressure. Operation of the pump is also enhanced, because the pump can continue to maintain a relatively constant delivery volume, independent of the pressure difference imposed across the pump. Efficiency of the pump is maintained, because the cracking pressure of the outlet check valve is not increased except when necessary to reduce a risk of free flow.

To explain the operation of the apparatus 200 in further detail, a complete pumping cycle will now be described. Fluid is first drawn in through the inlet check valve 214 by the diastolic action of the pump piston 206 within the pump chamber 208. During intake, the withdrawing pump piston causes the pressure of the pump chamber to fall below the inlet pressure, allowing the inlet check valve to open and allow fluid flow into the pump chamber. After completing intake, the pump begins the discharge cycle. The advancing pump piston causes the pump chamber to be pressurized, forcing the inlet check valve to close. When the pump chamber pressure exceeds the sum of the outlet pressure and the outlet check valve cracking pressure, the outlet check valve 216 will open, allowing fluid flow from the pump chamber to the outlet. At the completion of discharge, the pump piston begins to withdraw, causing the pump chamber pressure to drop below the outlet pressure, forcing the outlet check valve to close. Hence, reverse flow through the pump is also discouraged by the inlet and outlet check valves. If at any time during the pumping cycle, the inlet pressure is increased relative to this outlet, this pressure difference across the diaphragm 222 increases the cracking pressure of the outlet check valve, discouraging free flow through the outlet check valve.

The apparatus 200 thus provides inherent safety, in that for the outlet check valve 216 to open, pressure must originate from within the pump chamber 208. Positive inlet 210 to outlet 212 pressure differences originating outside the pump 204 will tend to increase the cracking pressure of the outlet check valve, providing resistance to free flow. Negative inlet to outlet pressure differences are isolated by the check valves 214, 216, providing resistance to backflow.

The area of the diaphragm 222 can be greater than the area of the ball 218 which is acted upon by the fluid. This helps to ensure that the force applied by the diaphragm to hold the outlet check valve 216 closed is larger than the hydrostatic force applied by the fluid to force the outlet check valve open. By making the area of the diaphragm large enough relative to the ball size, the outlet check valve can be forced closed if a predetermined pressure difference is exceeded. This may be a valuable feature in applications where it is desirable to shut off flow when there is a pressure imbalance.

Various ways of constructing the apparatus 200 will occur to one of skill in the art. For example, the housing 202 can be manufactured in a single piece, and the various channels (e.g. the inlet 210, outlet 212, pump chamber 208, and chambers for the inlet and outlet check valves 214, 216) formed in the housing or bored into the housing and plugged at one or both ends as necessary. Or, for example, a two-piece housing can be manufactured, placing the diaphragm and sealing gaskets between the two sections. Additionally, the ball valves may include chamfered or gasketed sealing surfaces or valve seats (e.g., at the junction of the pump chamber and outlet check valve chamber) to improve the sealing performance of the check valves. The housing may be fabricated from a variety of materials, including metal or plastic.

Figure 3:
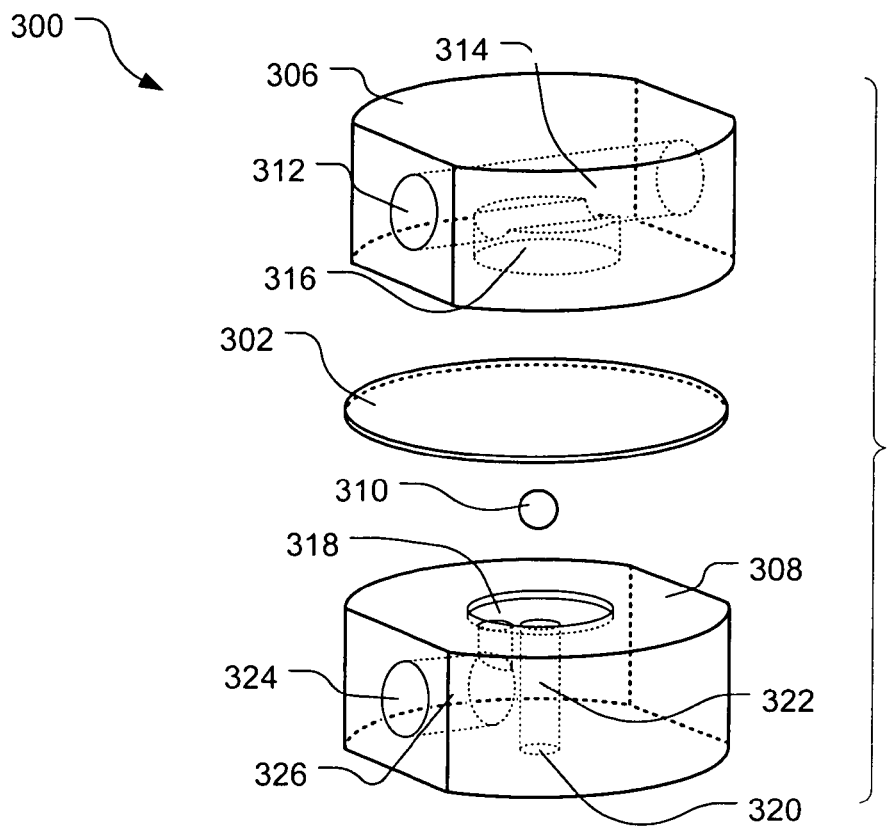
FIG. 3 is an exploded view of an apparatus for reducing free flow risk in accordance with a third embodiment of the present invention.
Figure 4:
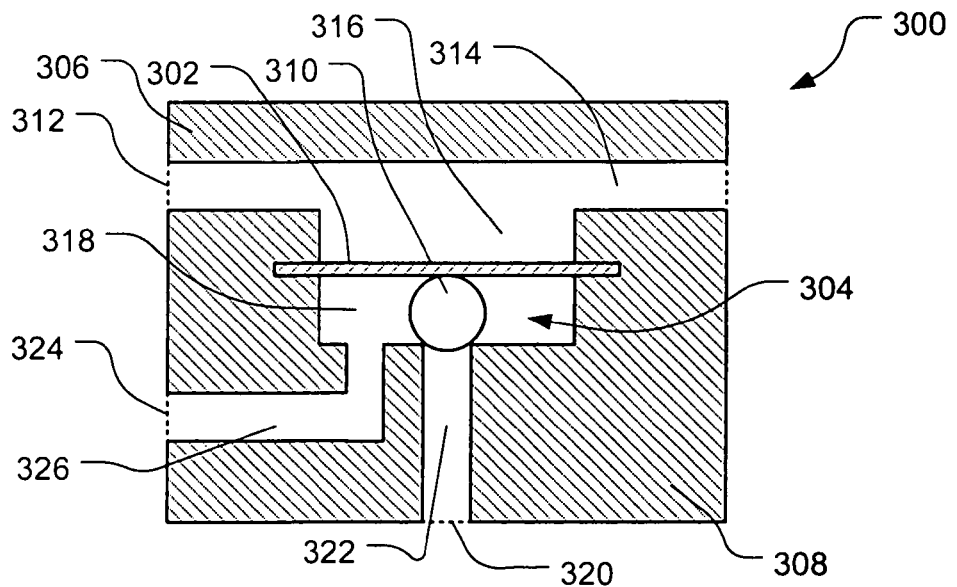
FIG. 4 is a cross-sectional view of the apparatus of FIG. 3.

An alternate arrangement of the pressure responsive member and flow restrictor is shown in FIGS. 3 and 4 in accordance with an embodiment of the present invention. As shown in FIGS. 3 and 4, the pressure responsive member, in the form of a diaphragm 302, and the flow restrictor, in the form of a ball valve, 304, can be integrated into a valve assembly 300, which can be separate from the pump (not shown).

As shown in FIG. 3 in an exploded view, the valve assembly may include a two part housing, having an upper housing 306 and lower housing 308. Disposed between the upper and lower housing is the diaphragm 302 and a ball 310.

The upper housing has a pump inlet pressure sensing port 312 which can be coupled to the pump inlet to sense the pressure at the pump inlet. For example, the pump inlet pressure sensing port may include internal threads or a flange to facilitate connection to the pump inlet. As illustrated here, the pressure sensing port includes a bore 314 which passes entirely through the upper housing, allowing the reservoir to be connected to one side of the bore and the pump inlet to the other side. Alternately, the bore may penetrate only partially into the upper housing, and be connected into the line between the reservoir and pump inlet with a tee junction. The bore is connected to an upper chamber 316, also formed in the upper housing.

The lower housing 308 has a lower chamber 318, which is substantially opposite the upper chamber 316. The lower chamber is coupled to a valve inlet 320 via an inlet bore 322, and coupled to a valve outlet 324 via an outlet bore 326. Similarly as described for the upper housing, the outlet bore may optionally pass entirely through the lower housing. The valve inlet may be coupled to the pump outlet, for example by including internal threads or a flange on the valve inlet. It should be noted that the upper chamber and lower chamber need not be perfectly aligned with each other, as long as portions of the chamber are opposite each other so the diaphragm is exposed to both the inlet and outlet pressure.

When assembled, as shown in FIG. 4 in cross-section view, the diaphragm 302 bears upon the ball 310. The ball valve 304 is formed through the cooperation of the inlet bore 322, ball, diaphragm, and outlet bore 326. The diaphragm provides a similar function as a spring in a ball valve (e.g., 214 and 216 in FIG. 2), setting an initial cracking pressure of the ball valve. When fluid pressure at the valve inlet 320 exceeds the initial cracking pressure of the ball valve, the ball will be raised, flexing the diaphragm, and fluid will be allowed to flow from the inlet, through the inlet bore, past the ball, and out the outlet bore to the valve outlet 324.

To help prevent free flow through a pump, the valve assembly 300 may be connected to the pump with the pump inlet coupled to (or through) the pump inlet pressure sensing port 312, and the pump outlet coupled to the valve inlet 320. This places the upper chamber 316 in a pressure transmitting relationship with the pump inlet, and the lower chamber 318 in a pressure transmitting relationship with the pump outlet. When a positive pressure difference is imposed on the pump inlet relative to the pump outlet, the pressure difference will be transmitted across the diaphragm 302, and onto the ball 310. The diaphragm thus provides a function of communicating the pressure difference to the valve 304, increasing the cracking pressure of the valve when a positive pressure difference is present. This will help to prevent free flow through the pump as has been discussed for other embodiments above.

Figure 5:
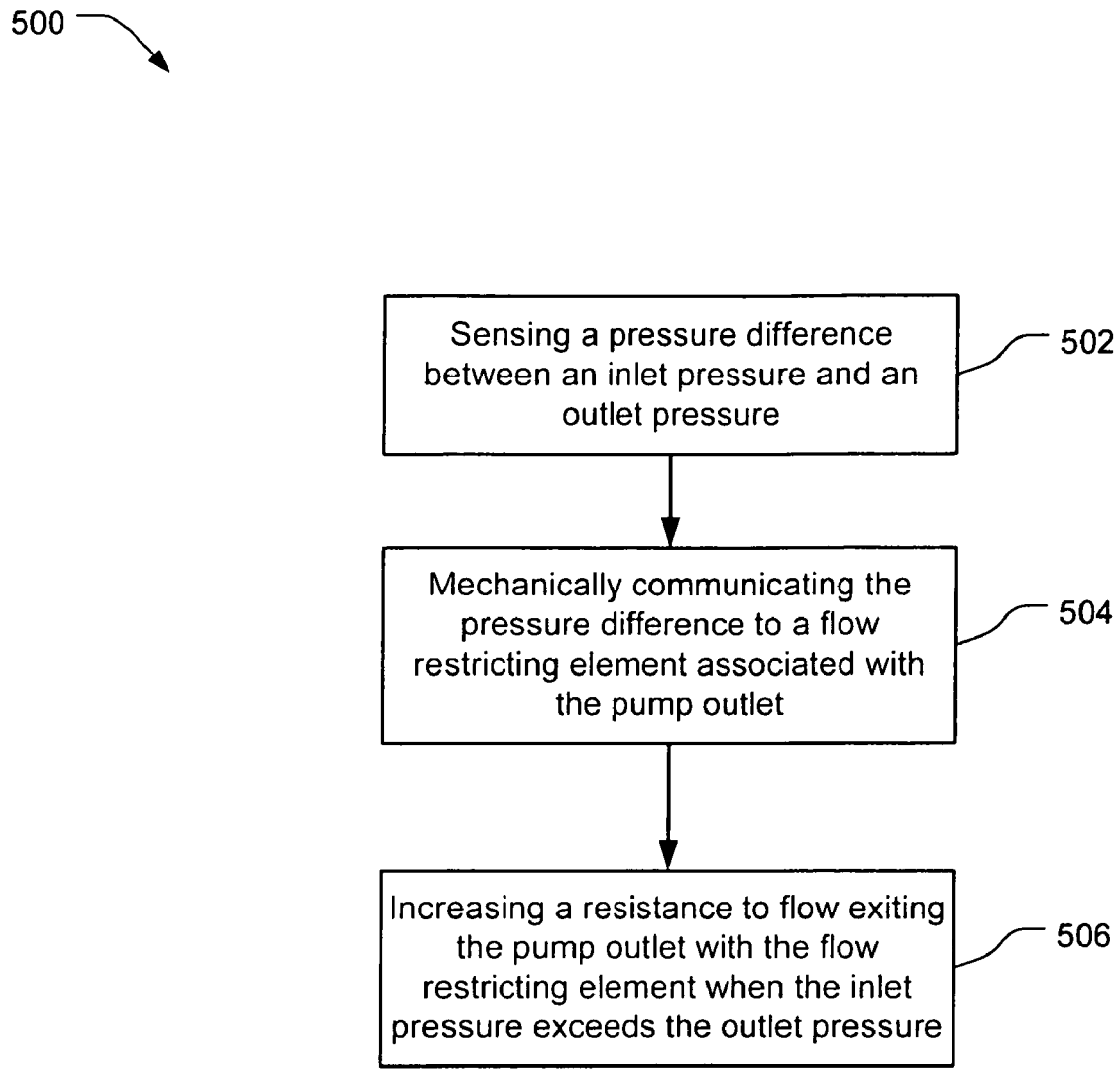
FIG. 5 is a flow chart of a method for reducing the risk of free flow through a pump in accordance with a fourth embodiment of the present invention.

Finally, a method for reducing the risk of free flow through a pump is illustrated in FIG. 5. The method 500 includes sensing 502 a pressure difference between the inlet and the outlet of a pump. For example, the pressure difference can be sensed by a pressure responsive member, such as a diaphragm or piston as described above.

The method can also include communicating 504 the pressure difference to a flow restricting element associated with the pump outlet. For example, the pressure difference may be communicated by mechanical movement of a piston or diaphragm mechanically coupled to the flow restricting element.

Finally, the method can also include increasing 506 resistance to flow exiting the pump outlet with the flow restricting element when the inlet pressure exceeds the outlet pressure. For example, the flow restricting element may be a valve (e.g., a pinch valve, blocking valve, or ball valve), placed within the outlet of the pump or coupled to the outlet of the pump, as described above. The valve can be closed in proportion to the pressure difference, for example by moving an element of the valve or increasing static pressure on an element of the value as described above. For example, as the pressure increases, the flow restricting element may be moved to reduce a cross-sectional area of a fluid channel, for example with a pinch valve as described above.

Reiterating to some extent, it can be appreciated from the foregoing that embodiments of the present invention can help to prevent free flow through a pump. For example, in the critical application of patient infusion systems, a risk of free flow exists when a fluid reservoir containing nutrients or drugs is pressurized relative to the patient. Embodiments of the present invention can help to prevent free flow under such circumstances based on the pressure difference between the inlet and outlet of a pump within the system. The sensed pressure can be mechanically translated into flow restriction to limit flow through the pump. The pressure sensing and flow restriction can be performed by relatively simple structures (e.g., a diaphragm or piston, and a pinch or ball valve). As high pressure differences between the inlet and outlet are present, increased flow restriction, including substantially complete shut off of flow exiting the pump can be accomplished. Hence, cost, reliability, and safety can all be enhanced over previously known techniques.

It is to be understood that the above-referenced arrangements are illustrative of the application for the principles of the present invention. It will be apparent to those of ordinary skill in the art that numerous modifications can be made without departing from the principles and concepts of the invention as set forth in the claims.

What is claimed is:

1. A method for reducing a risk of external pressure-induced free flow through a pump having an inlet and an outlet comprising:
    establishing a fluid communication between the pump inlet to a first side of a pressure responsive member;
    establishing a fluid communication between the pump outlet and a second side of the pressure responsive member independent of a pump outlet line;
    continuously sensing a pressure difference between an inlet pressure and an outlet pressure with the pressure responsive member;
    mechanically communicating the pressure difference to a flow restricting element associated with the pump outlet line, wherein the flow restricting element does not inhibit the fluid communication between the pump outlet and the pressure responsive member; and
    activating the flow restricting element when the inlet pressure exceeds the outlet pressure to increase a resistance to a fluid flow through the pump outlet line in proportion to the pressure difference between the inlet pressure and the outlet pressure.

2. The method of claim 1 wherein activating the flow restricting element comprises mechanically moving an element of the flow restricting element in proportion to the pressure difference.

3. The method of claim 1 wherein activating the flow restricting element comprises directly applying the pressure difference to an element of the flow restricting element.

4. The method of claim 1 wherein increasing a resistance to flow exiting the pump outlet line further comprises limiting the flow exiting the pump outlet in proportion to the pressure difference.

5. The method of claim 1 wherein increasing a resistance to flow exiting the pump outlet further comprises moving the flow restricting element to reduce a cross-sectional area of the pump outlet line.

6. The method of claim 1 further comprising increasing a resistance to flow through the pump outlet line without affecting the continuous sensing of the pressure differential between the inlet pressure and an outlet pressure by the pressure responsive member.

7. The method of claim 1 wherein increasing a resistance to flow exiting the pump outlet line further comprises completely blocking flow from exiting the pump outlet when the inlet pressure exceeds the outlet pressure.

8. An apparatus for reducing free flow risk comprising:
    a pump having a pump inlet and pump outlet, configured to transfer fluid received from the pump inlet to the pump outlet;
    a pressure responsive member in fluid communication with the pump inlet and with the pump outlet independent of a pump outlet line, the pressure responsive member operating to respond to a pressure difference between the pump inlet and the pump outlet; and
    a flow restrictor mechanically coupled to the pressure responsive member that limits fluid flow through the pump outlet line, wherein the flow restrictor does not inhibit the fluid communication between the pump outlet and the pressure responsive member and is configured to increase a resistance to a fluid flow through the pump outlet line in proportion to the pressure difference between the pump inlet and the pump outlet when an inlet pressure exceeds an outlet pressure.

9. The apparatus of claim 8 wherein the flow restrictor is further configured to limit fluid flow exiting the pump outlet in proportion to the pressure difference.

10. The apparatus of claim 8 wherein the flow restrictor is further configured to substantially prevent fluid flow exiting the pump outlet when the inlet pressure exceeds the outlet pressure.

11. The apparatus of claim 8 wherein the flow restrictor comprises a pinch valve.

12. The apparatus of claim 8 wherein the pressure responsive member comprises a moveable element disposed within a chamber and coupled to the flow restrictor, wherein a first side of the moveable element defines a first part of the chamber, the first part of the chamber in pressure transmitting relation with the pump inlet, and wherein a second side of the moveable element defines a second part of the chamber, the second part of the chamber in pressure transmitting relation with the pump outlet, whereby the pressure difference causes the moveable element to translate within the chamber.

13. The apparatus of claim 12 further comprising a spring disposed within the first part of the chamber so as to provide a shut off bias of the flow restrictor.

14. The apparatus of claim 12 wherein the moveable element is a diaphragm mounted within the chamber.

15. The apparatus of claim 12 wherein the moveable element is a piston slidably mounted within the chamber.

16. An apparatus for reducing free flow risk through a pump having a pump inlet and a pump outlet comprising:
    means for sensing a pressure difference between the pump inlet and the pump outlet;
    means for mechanically communicating the sensed pressure difference to a flow restricting element associated with a pump outlet line; and
    means for increasing a resistance to fluid flow through the pump outlet line through the flow restricting element that is responsive to the means for mechanically communicating the sensed pressure difference when an inlet pressure exceeds an outlet pressure, wherein the flow restricting element does not inhibit the means for sensing a pressure difference and is configured to increase the resistance to flow in proportion to the sensed pressure difference.

* * * * *